United States Patent
Lappin

(10) Patent No.: US 10,603,053 B2
(45) Date of Patent: Mar. 31, 2020

(54) METHOD OF USING A COMBINATION DRIVER/ANTI-ROTATION HANDLE FOR SHOULDER ARTHROPLASTY

(71) Applicant: DePuy Synthes Products, Inc., Raynham, MA (US)

(72) Inventor: Kyle E. Lappin, Fort Wayne, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 211 days.

(21) Appl. No.: 15/690,713

(22) Filed: Aug. 30, 2017

(65) Prior Publication Data

US 2017/0360457 A1 Dec. 21, 2017

Related U.S. Application Data

(60) Division of application No. 13/363,583, filed on Feb. 1, 2012, now Pat. No. 9,763,679, which is a
(Continued)

(51) Int. Cl.
*A61B 17/16* (2006.01)
*A61B 17/17* (2006.01)
(Continued)

(52) U.S. Cl.
CPC ...... *A61B 17/1684* (2013.01); *A61B 17/1631* (2013.01); *A61B 17/1778* (2016.11);
(Continued)

(58) Field of Classification Search
CPC ............ A61B 17/1684; A61B 17/1778; A61B 17/1631; A61B 17/1633; A61B 17/16;
(Continued)

(56) References Cited

U.S. PATENT DOCUMENTS 2,487,203 A 11/1949 Wilbur
3,855,638 A 12/1974 Pilliar
(Continued)

FOREIGN PATENT DOCUMENTS

CH 693446 8/2003
EP 1 639 949 3/2006
(Continued)

OTHER PUBLICATIONS

Affiniti Glenoid—Surgical Technique. Tornier, Dec. 2008, faculty.washington.edu/alexbert/Shoulder/Surgery/TornierAffinititechnique.pdf; last visited on May 23, 2019 (Year: 2008).*
(Continued)

*Primary Examiner* — David W Bates
*Assistant Examiner* — Marcela I Shirsat
(74) *Attorney, Agent, or Firm* — Maginot, Moore & Beck, LLP

(57) ABSTRACT

A method of preparing a shoulder to receive a glenoid component includes accessing a glenoid of a shoulder, rotationally coupling a distal portion of a combination device to an instrument, applying a torque to a proximal portion of the combination device, transferring the applied torque from the proximal portion to the distal portion through a pivotable connection, rotating the instrument using the transferred applied torque, and reaming a portion of the glenoid with a rotating reaming section of the instrument using the transferred applied torque.

10 Claims, 10 Drawing Sheets

Related U.S. Application Data continuation-in-part of application No. 13/051,026, filed on Mar. 18, 2011, now Pat. No. 9,820,758.

(51) Int. Cl.
  *B25B 13/48* (2006.01)
  *B25B 23/00* (2006.01)

(52) U.S. Cl.
  CPC ......... *A61B 17/1633* (2013.01); *B25B 13/481* (2013.01); *B25B 23/0028* (2013.01); *B25B 23/0042* (2013.01)

(58) Field of Classification Search
  CPC . A61B 17/1662; A61B 17/1615; B25B 51/02; B25B 51/108; B25B 51/10; B25B 51/107; B25B 23/0028; B25B 23/0035; B25B 23/0014; B25B 23/16; B25B 23/0042; B25B 23/007; B25B 13/481; B25B 13/461; B23B 2251/14; B23B 2251/60; B23B 2251/606
  USPC ....... 606/79, 80–81, 91, 170, 180; 81/57.26, 81/57.27, 177.6, 177.7, 177.75, 177.8; 408/127, 223, 224
  See application file for complete search history.

(56) References Cited

U.S. PATENT DOCUMENTS

| | | | |
|---|---|---|---|
| 4,030,143 | A | 6/1977 | Elloy et al. |
| 4,964,865 | A | 10/1990 | Burkhead et al. |
| 5,030,219 | A | 7/1991 | Matsen, III et al. |
| 5,080,673 | A | 1/1992 | Burkhead et al. |
| 5,180,384 | A | 1/1993 | Mikhail |
| 5,324,295 | A | 6/1994 | Shapiro |
| 5,489,310 | A | 2/1996 | Mikhail |
| 5,800,551 | A | 9/1998 | Williamson et al. |
| 5,919,195 | A | 7/1999 | Wilson et al. |
| 6,010,535 | A | 1/2000 | Shah |
| 6,045,302 | A | 4/2000 | Orr |
| 6,228,900 | B1 | 5/2001 | Shen et al. |
| 6,245,074 | B1 | 6/2001 | Allard et al. |
| 6,281,264 | B1 | 8/2001 | Salovey et al. |
| 6,364,910 | B1 | 4/2002 | Shultz et al. |
| 6,379,386 | B1 | 4/2002 | Resch et al. |
| 6,679,916 | B1 | 1/2004 | Frankle et al. |
| 6,699,289 | B2 | 3/2004 | Iannotti et al. |
| 6,783,549 | B1 | 8/2004 | Stone et al. |
| 7,294,133 | B2 | 11/2007 | Zink et al. |
| 7,329,284 | B2 | 2/2008 | Maroney et al. |
| 7,338,498 | B2 | 3/2008 | Long et al. |
| 7,604,665 | B2 | 10/2009 | Iannotti et al. |
| 8,764,836 | B2 | 7/2014 | De Wilde et al. |
| 2002/0082702 | A1 | 6/2002 | Resch et al. |
| 2003/0125809 | A1 | 7/2003 | Iannotti et al. |
| 2004/0097947 | A1 | 5/2004 | Wolford et al. |
| 2004/0193168 | A1 | 9/2004 | Long et al. |
| 2005/0278030 | A1 | 12/2005 | Tornier et al. |
| 2006/0015112 | A1* | 1/2006 | McGovern ............ A61B 17/164 606/80 |
| 2006/0020344 | A1 | 1/2006 | Shultz et al. |
| 2006/0069444 | A1 | 3/2006 | Deffenbaugh |
| 2006/0111787 | A1 | 5/2006 | Bailie et al. |
| 2006/0195194 | A1 | 8/2006 | Gunther |
| 2006/0276905 | A1 | 12/2006 | Calamel |
| 2007/0016304 | A1 | 1/2007 | Chudik |
| 2007/0038302 | A1 | 2/2007 | Shultz et al. |
| 2007/0055249 | A1 | 3/2007 | Jensen et al. |
| 2007/0260321 | A1 | 11/2007 | Stchur |
| 2008/0306600 | A1 | 12/2008 | Huebner |
| 2009/0270993 | A1 | 10/2009 | Maisonneuve et al. |
| 2010/0070044 | A1 | 3/2010 | Maroney et al. |
| 2010/0087876 | A1 | 4/2010 | Gunther |
| 2010/0161065 | A1 | 6/2010 | Williams, Jr. et al. |
| 2010/0249938 | A1 | 9/2010 | Gunther et al. |
| 2010/0274359 | A1 | 10/2010 | Brunnarius et al. |
| 2010/0331990 | A1 | 12/2010 | Mroczkowski et al. |
| 2011/0012318 | A1 | 1/2011 | Northwood |
| 2011/0028977 | A1 | 2/2011 | Rauscher et al. |
| 2011/0035013 | A1 | 2/2011 | Winslow et al. |
| 2012/0130499 | A1 | 5/2012 | Long |
| 2013/0123930 | A1 | 5/2013 | Burt |

FOREIGN PATENT DOCUMENTS

| | | |
|---|---|---|
| EP | 1 815 825 | 8/2007 |
| FR | 2704747 | 11/1994 |
| FR | 2940607 | 7/2010 |
| GB | 2 406 278 | 3/2005 |
| JP | H1128256 | 5/1999 |
| JP | 2003230584 | 8/2003 |
| JP | 2009501026 | 1/2009 |
| JP | 2009518077 | 5/2009 |
| JP | 5123336 | 11/2012 |
| WO | 2010150223 | 12/2010 |
| WO | 2011005205 | 1/2011 |

OTHER PUBLICATIONS

Warner, Jon J.P., M.D. et al, "Articular Contact Patterns of the Normal Glenohumeral Joint," Journal of Shoulder and Elbow Surgery, Jul./Aug. 1998, vol. 7, No. 4, pp. 381-388. ( 8 pages).

Westerhoff, P., et al., "In Vivo Measurement of Shoulder Joint Loads During Activities of Daily Living," Journal of Biomechanics 42 (2009), pp. 1840-1849. (10 pages).

Williams, Gerald R., Jr., M.D., and Iannotti, Joseph P., M.D. PhD., "Options for Glenoid Bone Loss: Composites of Prosthetics and Biologics," Journal of Shoulder and Elbow Surgery, Sep./Oct. 2007, vol. 16, No. 5S, pp. 267S-272S. (6 pages).

Wirth, Michael A., M.D. and Rockwood, Charles A., Jr., M.D., "Complications of Shoulder Arthroplasty," Clinical Orthopaedics and Related Research, Oct. 1994, No. 307, pp. 47-69. ( 23 pages).

Wirth, Michael A. and Rockwood, Charles A., Jr., "Current Concepts Review—Complications of Total Shoulder-Replacement Arthroplasty," Journal of Bone & Joint Surgery, Apr. 1996, vol. 78-A, No. 4, pp. 603-616. (15 pages).

Australian Examination Report corresponding to application No. 2012231298, dated Sep. 17, 2015 (4 pages).

Chinese Search Report corresponding to application No. 201280023890.7, dated Jun. 5, 2015 (2 pages).

Chinese Search Report corresponding to application No. 201280023936.5, dated Aug. 25, 2015 (2 pages.

Maisonobe et al.; Finding the Circle that Best Fits a Set of Points; Oct. 25, 2007; 11 pages.

Chinese Supplementary Search Report corresponding to application No. 201280023936.5, dated Apr. 25, 2016 (2 pages).

Extended European Search Report corresponding to European Patent Application 12760666.3, dated May 13, 2014 (10 pages).

Japanese Office Action corresponding to application No. 2013-558132, dated Jan. 12, 2016 (5 pages).

Japanese Office Action corresponding to application No. 2014-501145, dated Jan. 19, 2016 (4 pages).

Matsen III, Fredereick A., et al., "Shoulder Arthroplasty: The Socket Perspective," Journal of Shoulder and Elbow Surgery, Oct. 2007; 1: 24S-247S (7 pages).

Piasecki et al., Review Article: "Glenoid Bone Deficiency in Recurrent Anterior Shoulder Instability: Diagnosis and Management," JAm Acad. Ortho. Surg. 2009, vol. 17, pp. 482-493 (12 pages).

International Preliminary Report on Patentability in corresponding PCT application PCT/US2012/029034, report dated Sep. 24, 2013 (7 pages).

Extended European Search Report corresponding to European Application No. 12760274.6, dated Jun. 27, 2014 (6 pages).

Extended European Search Report corresponding to European Patent Application No. 12760199.5, dated Aug. 7, 2014 (6 pages).

(56) References Cited

OTHER PUBLICATIONS

Extended European Search Report corresponding to European Patent Application No. 16167719.0-1654, dated Sep. 6, 2016 (6 pages).
Dictionary Definition for "best-fit", English Oxford Dictionaries Online, Accessed Oct. 3, 2016.
Dictionary Definition for "guide", English Oxford Dictionaries Online, Accessed Oct. 3, 2016.
Japanese Office Action corresponding to application No. 2013-016623, dated Dec. 6, 2016 (4 pages).
Jeske, H.C., et al., "Normal glenoid rim anatomy and the reliability of shoulder instability measurements based on intrasite correlation," Surg. Radiol. Anat., vol. 31, pp. 623-625, Mar. 2009 (3 pages).
International Search Report in corresponding PCT Application (i.e., PCT/US2012/029021), dated Jul. 11, 2012 (4 pages).
European Search Report and European Search Opinion in corresponding European patent application EP 13151417.6, dated Mar. 20, 2013 (7 pages).
Antuna et al., "Glenoid revision surgery after total shoulder arthroplasty," Journal of Shoulder Elbow Surgery, 2001, pp. 217-224, vol. 10, Rochester, MN (8 pages).
Boileau P, Walch G., "The three dimensional geometry of the proximal humerus. Implications for the surgical technique and prosthetic design." J. Bone Joint Surg Br 1997;79-B:857-65. doi:10.1302/0301-620X.79B5.7579 (9 pages).
Boyer PJ, Massimini DF, Gill TJ, Papannagari R, Stewart SL, Warner JP, Li G., "In vivo articular cartilage contact at the glenohumeral joint: preliminary report." J. Orthop Sci. 2008;13:359-65.doi:10.1007/s00776-008-1237-3 (7 pages).
Bryce CD, Davison AC, Lewis GS, Wang , Flemming DJ, Armstrong AD., "Two dimensional glenoid version measurements vary with coronal and sagittal scapular rotation." J Bone Joint Surg Am. 2010;92-692-9.doi.10.2106/JBJS.I.00177 (8 pages).
Codsi et al., "Normal glenoid vault anatomy and validation of a novel glenoid implant shape," Journal of Shoulder Elbow Surgery, May/Jun. 2008, pp. 471-478, vol. 17, Austria (8 pages).
Couteau B, Mansat , Darmana R, Mansat M., Egan J., "Morphological and mechanical analysis of the glenoid by 3D geometric reconstruction using computed tomography." Clin Biomech 2000;15(suppl1):8-12.doi:10.1016/S0268-0033(00)00052-8 (5 pages).
Couteau B, Mansat P. Estivales E, Darmana R. Mansat M., Egan J., "Finite element analysis of the mechanical behavior of a scapula implanted with a glenoid prosthesis." Clin Biomech 2001;16:566-75.doi:10.1016/S0268-0033(01)00029-8 (10 pages).
Couteau B, Mansat P, Mansat M, Darmana R, Egan J., "In vivo characterization of glenoid with use of computed tomography." J Shoulder Elbow Surg 2001;116-22 (7 pages).
De Wilde LF, Verstraeten T, Speeckaert W, Karelse A, "Reliability of the glenoid plane." J Shoulder Elbow Surg.2010;19:414-22. doi:10.1016/j.jse.2009.10.005. (9 pages).
Graichen H, Hinterwimmer S, von Eisenhart-Rothe R, Vogl T. Englmeier KH, Eckstein F., "Effect of abducting and adducting muscle acitivity on glenohumeral translation, scapular kinematics and subacromial space width in vivo." Journal of Biomechanics 2005;38:755-60. doi:10.1016/j.jbiomech.2004.05.020. (6 pages).
Graichen H, Stammberger T. Bonel H, Karl-Hans E, Reiser M, Eckstein F., "Glenohumeral translation during active and passive elevation of the shoulder—a 3D open-MRI study." Journal of Biomechanics 2000;33:609-13.doi:10.1016/S0021-9290(99)00209-2. (5 pages).
Harryman DT, Sidles JA, Harris SL, Lippitt SB, Matsen FA., "The effect of articular conformity and the size of the humeral head component on laxity and motion after glenohumeral arthroplasty." J. Bone Joint Surg Am 1995;77-A:555-63.No doi found. (10 pages).
Huysmans PE, Haen PS, Kidd M, Dhert WJ, Willems JW., "The shape of the inferior part of the glenoid: a cadaveric study." J Shoulder Elbow Surg. 15(6):759-63. doi:10.1016/j.jse.2005.09.001 (5 pages).
Karelse et al., "The Pillars of the Scapula", Clinical Anatomy, 2007, pp. 392-399, vol. 20, Belgium (8 pages).

Erichsen, "Injuries of the Nervous System on Railway and Other Injuries of the Nervous System", The Classic Article in Clinical Orthopaedics and Related Research, Mar. 1997, pp. 47-51, No. 458, Walton and Moberly, London (5 pages).
Iannotti JP, Gabriel JP, Schneck SL, Evans BG, Misra S., "The normal glenohumeral relationships. An anatomical study of one hundred and forty shoulders." J. Bone Joint Surg Am. 1992;74(4); 491-500. No doi found. (11 pages).
Karduna AR, Williams GR, Williams JL, Ianotti JP., "Glenohumeral Joint translations before and after total shoulder arthroplasty." J Bone Joint Surg 1997;79-A,1166-74. No doi found. (10 pages).
Lee SB, Kim KJ, O'Driscoll SW, Morrey BF, an KN., "Dynamic glenohumeral stability provided by the rotator cuff muscles in the mid-range and end-range of motion." A study in cadavera. J. Bone Joint Surg Am. 2000;82(6):849-57. No doi found (10 pages).
Lewis GS, Bryce CD, Davison AC, Hollenbeak CS, Piazza SJ, Armstrong AD., "Location of the optimized centerline of the glenoid vault: a comparison of two operative techniques with use of three-dimensional computer modeling." J Bone Joint Surg Am, 2010;92:1188-94. doi:10-2106/JBJS.I.00131. (8 pages).
Mahfouz M, Nicholson G, Komistek R, Hovis D, Kubo M., "In vivo determination of the dynamics of normal, rotator cuff-deficient, total, and reverse replacement shoulders." J Bone Joint Surg Am. 2005;87 Suppl 2:107-13. doi:10.2106/JBJS.E.00483 (8 pages).
Massimini DF, Li G, Warner JP, "Glenohumeral contact kinematics in patients after total shoulder arthroplasty." J Bone Joint Surg Am. Apr. 2010;92(4):916-26. doi:10.2106/JBJS.H.01610. (12 pages).
Matsen FA., "Early effectiveness of shoulder arthroplasty for patients who have primary glenohumeral degenerative joint disease." J Bone and Joint Surg 1996;78-A:260-4. No doi found. (6 pages).
Nyffeler RW, Sheikh R, Atkinson TS, Jacob HA, Favre P, Gerber C., "Effects of glenoid component version on humeral head displacement and joint reaction forces: an experimental study." J Shoulder Elbow Surg. 2006;15:625-9. doi:10.1016/j.jse.2005.09.016. (5 pages).
Nyffeler RW, Werner CM, Sukthankar A, Schmid MR, Gerber C., "Association of a large lateral extension of the acromion with rotator cuff tears." J. Bone Joint Surg Am. 2006;88-800-5. No doi found (7 pages).
Pappas GP, Blemker SS, Beaulieu CF, McAdams TR, Whalen ST, Gold GE., "In vivo anatomy of the Neer and Hawkins sign positions for shoulder impingement." J Shoulder Elbow Surg 2006;15:40-9. doi:10.1016/j.ise.2005.04.007. (10 pages).
Pearl ML, Krurtz S., "Geometric analysis of commonly used prosthetic systems for proximal humeral replacement." J Bone Joint Surg 1999;81-A:660-71. No doi found (13 pages).
Scalise JJ, Codsi MJ, Bryan J, Brems JJ, Iannotti JP., "The influence of three-dimensional computed tomography images of the shoulder in preoperative planning for total shoulder arthroplasty." J Bone Joint Surg Am. 2008;90:2438-45.doi:10.2106/JBJS.G.01341. (9 pages).
Schiffern SC, Rozencwaig R, Antoniou J, Richardson ML, Matsen FA III., "Anteroposterior centering of the humeral head on the glenoid in vivo." Am J Sports Med. 2002;30(3):382-7. No doi found. (7 pages).
Soslowsky LJ, Flatow EL, Bigliani LU, Pawluk RJ, Ateshian GA, Mow VC., "Quantitation of in situ contact areas at the glenohumeral joint: a biomechanical study." J Orthop Res. 1992;10:524-34. doi:10.1002/jor.1100100407. (11 pages).
Takase K, Yamamoto K, Imakiire A, Burkhead WZ Jr., "The radiographic study in the relationship of the glenohumeral joint." J Orthop Res. 2004;22:298-305. doi:10.1016/S0736-0266(03)00187-6 (8 pages).
Tokgoz N, Kanatli U, Voyvoda NK, Gultekin S, Bolukbasi S. Tali ET., "The relationship of glenoid and humeral version with supraspinatus tendon tears." Skeletal Radion. 2007;36:509-14. No doi found. (6 pages).
Werner CML, Weishaupt D, Blumenthal S, Curt A, Favre P, Gerber C., "Effect of experimental suprascapular nerve block on active glenohumeral translations in vivo." J Orthop Res 2006;24:491-500. doi:10.1002/jor.20011. (10 pages).
Bey, Michael J., et al., " Measuring Dynamic In-Vivo Glenohumeral Joint Kinematics: Technique and Preliminary Results," Journal of Biomechanics 41 (2008), pp. 711-714. (4 pages).

(56) References Cited

OTHER PUBLICATIONS

Chant, Chris B., et al., "Humeral Head Retroversion in Competitive Baseball Players and Its Relationship to Glenohumeral Rotation Range of Motion," Journal of Orthopaedic & Sports Physical Therapy, Sep. 2007, vol. 37, No. 9, pp. 514-520. (7 pages).
Conzen, Annemarie and Eckstein, Felix, MD, "Quantitative Determination of Articular Pressure in the Human Shoulder Joint," Journal of Shoulder and Elbow Surgery, vol. 9, No. 3, May/Jun. 2000, pp. 196-204. (9 pages).
De Wilde, Lieven F. MD, et al., "Glenohumeral Relationship in the Transverse Plane of the Body," Journal of Shoulder and Elbow Surgery, vol. 12, No. 3, May/Jun. 2003, pp. 260-267. (8 pages).
De Wilde, L.F., et al., "About the Variability of the Shape of the Glenoid Cavity," Surgical and Radiologic Anatomy (2004) 26; pp. 54-59. (6 pages).
Fleiss, Joseph L., "Analysis of Data From Multiclinic Trials," Controlled Clinical Trials 7: 267-275 (1986). (9 pages).
Hertel, Ralph M.D., "Geometry of the Proximal Humerus and Implications for Prosthetic Design," Journal of Shoulder and Elbow Surgery, Jul./Aug. 2002, vol. 11, No. 4, pp. 331-338. (8 pages).
Mansat, M. and Fourcade, D., "Preoperative Planning in Shoulder Prosthesis," Acta Orthopaedica Belgica (1995) vol. 61—Suppl. Jan. 1995. (6 pages).
Middernacht, Bart, MD, et al., "Consequences of Scapular Anatomy for Reversed Total Shoulder Arthroplasty," Clinical Orthopaedics and Related Research (2008) 466: 1410-1418. (9 pages).
Moon, P. and Spencer, D.E., Rectangular Coordinates (x,y,z). Field Theory Handbook, Including Coordinate Systems, Differential Equations, and Their Solutions (1988), New York: Springer-Verlag, pp. 9-11 (Table 1.01). (3 pages).
Pearl, Michael L., M.D. and Volk, Albert G., M.D., "Coronal Plane Geometry of the Proximal Humerus Relevant to Prosthetic Arthroplasty," Journal of Shoulder and Elbow Surgery, vol. 5, No. 4, Jul./Aug. 1996, pp. 320-326. (7 pages).
Pearl, ML and Volk, AG, "Retroversion of the Proximal Humerus in Relationship to Prosthetic Replacement Arthroplasty," Journal of Shoulder and Elbow Surgery, Jul. 1995, vol. 4, No. 4, pp. 286-289. (4 pages).
Randelli, M., M.D. and Gambrioli, P.L., M.D., "Glenohumeral Osteometry by Computed Tomography in Normal and Unstable Shoulders," Clinical Orthopaedics and Related Research, No. 208, Jul. 1986, pp. 151-156. (6 pages).
Robertson, Douglas D., M.D., et al., "Three-Dimensional Analysis of the Proximal Part of the Humerus: Relevance to Arthroplasty," The Journal of Bone and Joint Surgery, vol. 82-A,No. 11, Nov. 2000, pp. 1594-1602. (9 pages).
Rougraff, Bruce T., M.D., et al., " Does Length of Symptoms Before Diagnosis of Sarcoma Affect Patient Survival?" Clinical Orthopaedics and Related Research (2007), No. 462, pp. 181-189. (9 pages).
Shrout, Patrick E. and Fleiss, Jospeh L., "Intraclass Correlations: Uses in Assessing Rater Reliability," Psychological Bulletin, 1979, vol. 86, No. 2, pp. 420-428. (9 pages).
Soslowsky, Louis J., Ph.D. et al, "Articular Geometry of the Glenohumeral Joint," Clinical Orthopaedics and Related Research, No. 285, Dec. 1992, pp. 181-190. (10 pages).
Tetreault, Patrice, et al., "Glenoid Version and Rotator Cuff Tears," Journal of Orthopaedic Research 22 (2004) pp. 202-207. (6 pages).
Australian Examination Report No. 1 for AU Application No. 2013200329, dated Aug. 18, 2017 (6 pages).

\* cited by examiner

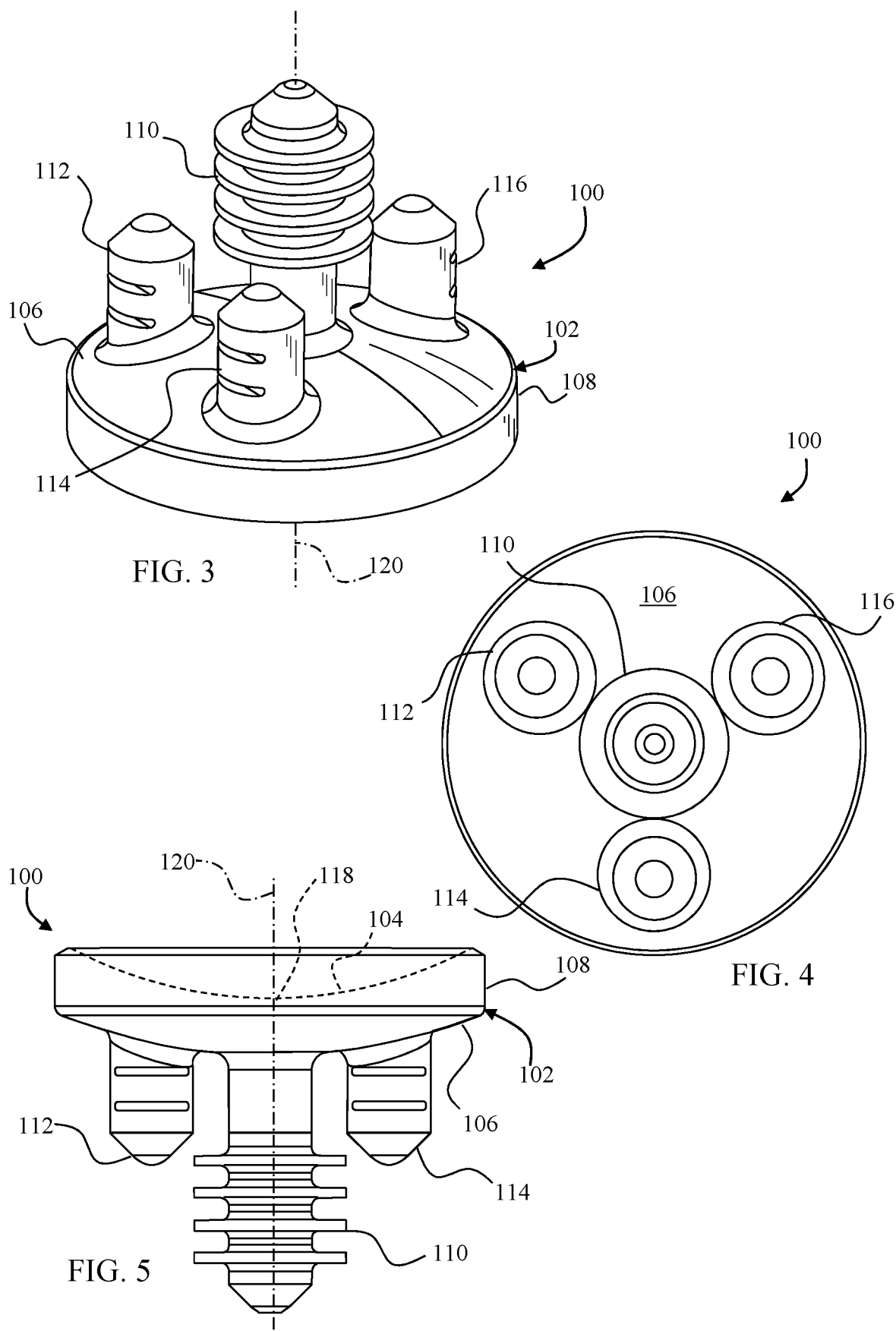

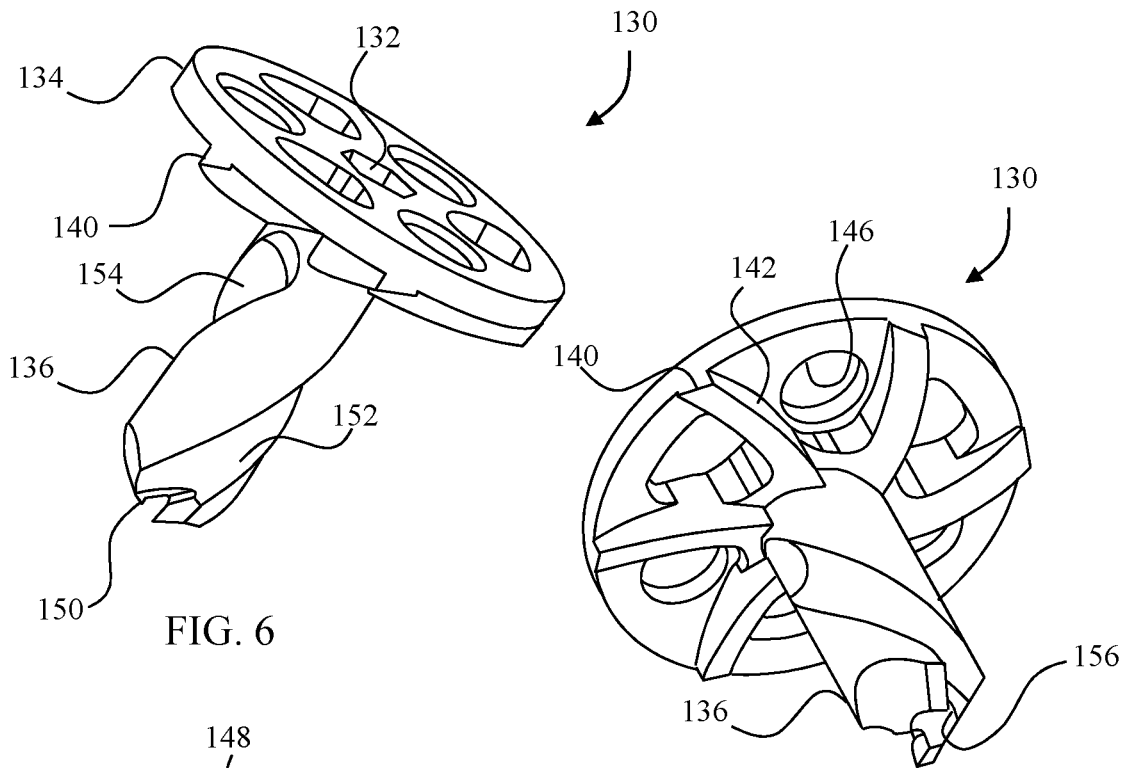
FIG. 6
FIG. 7
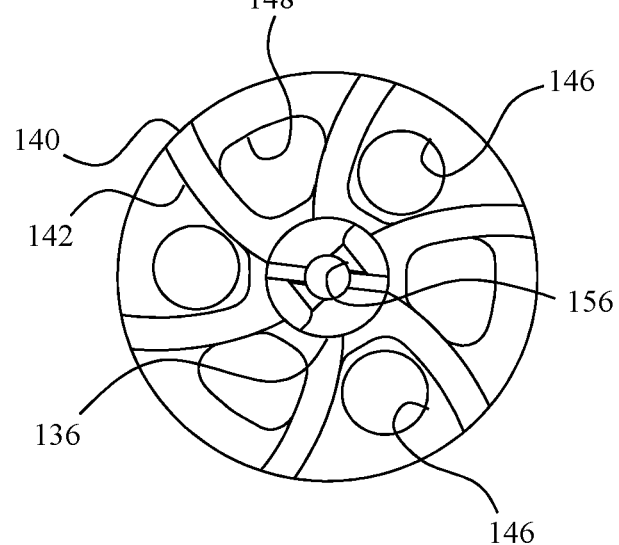
FIG. 8
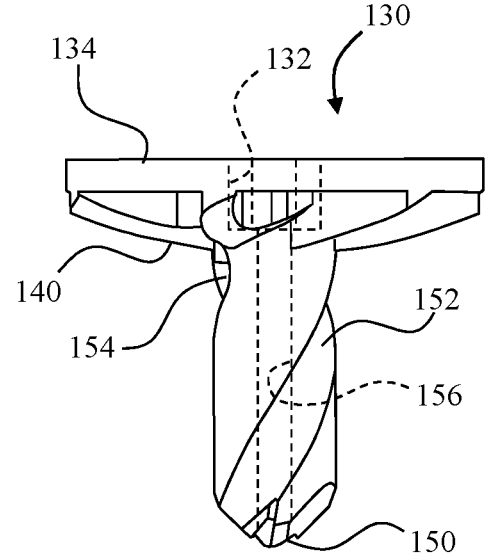
FIG. 9

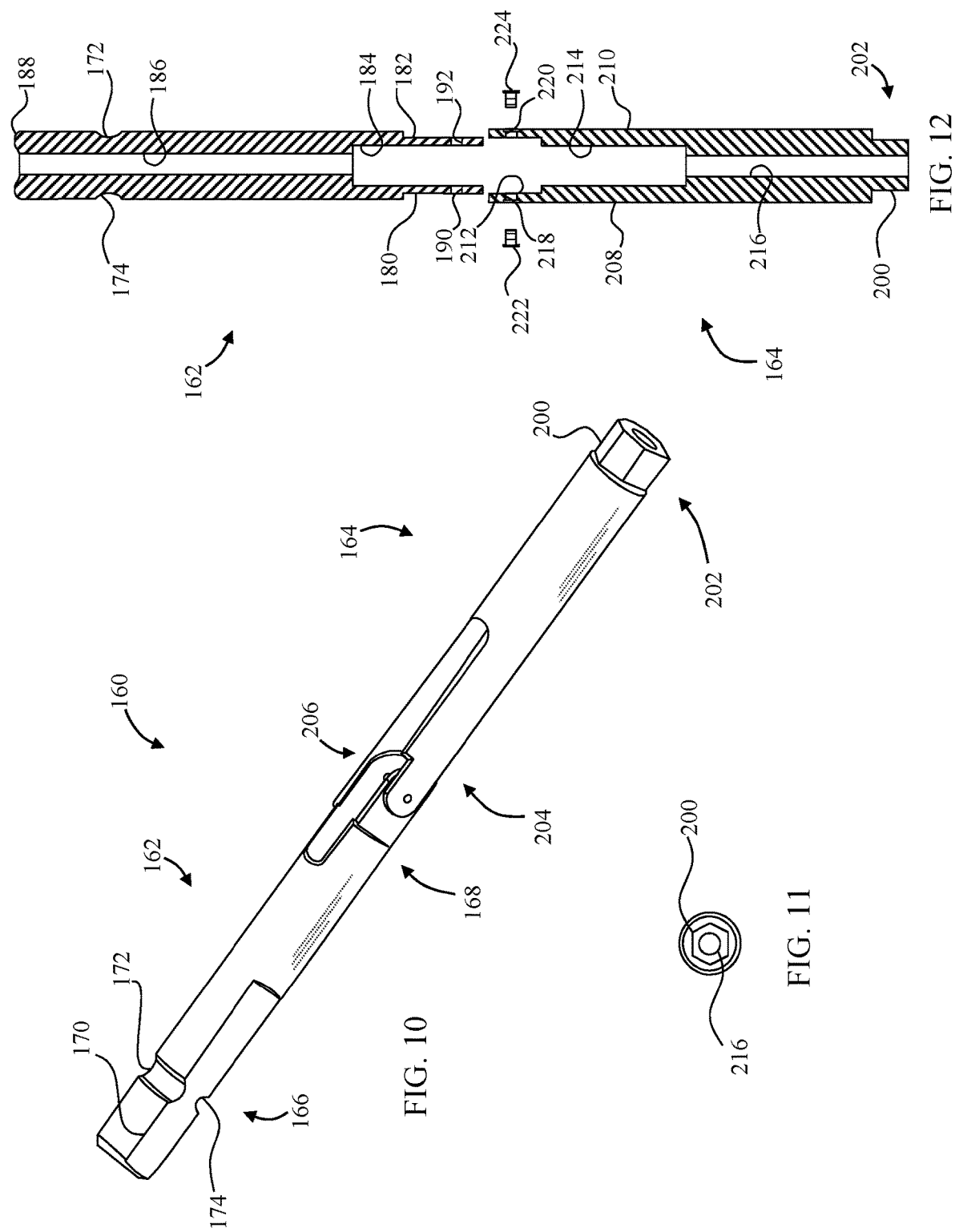

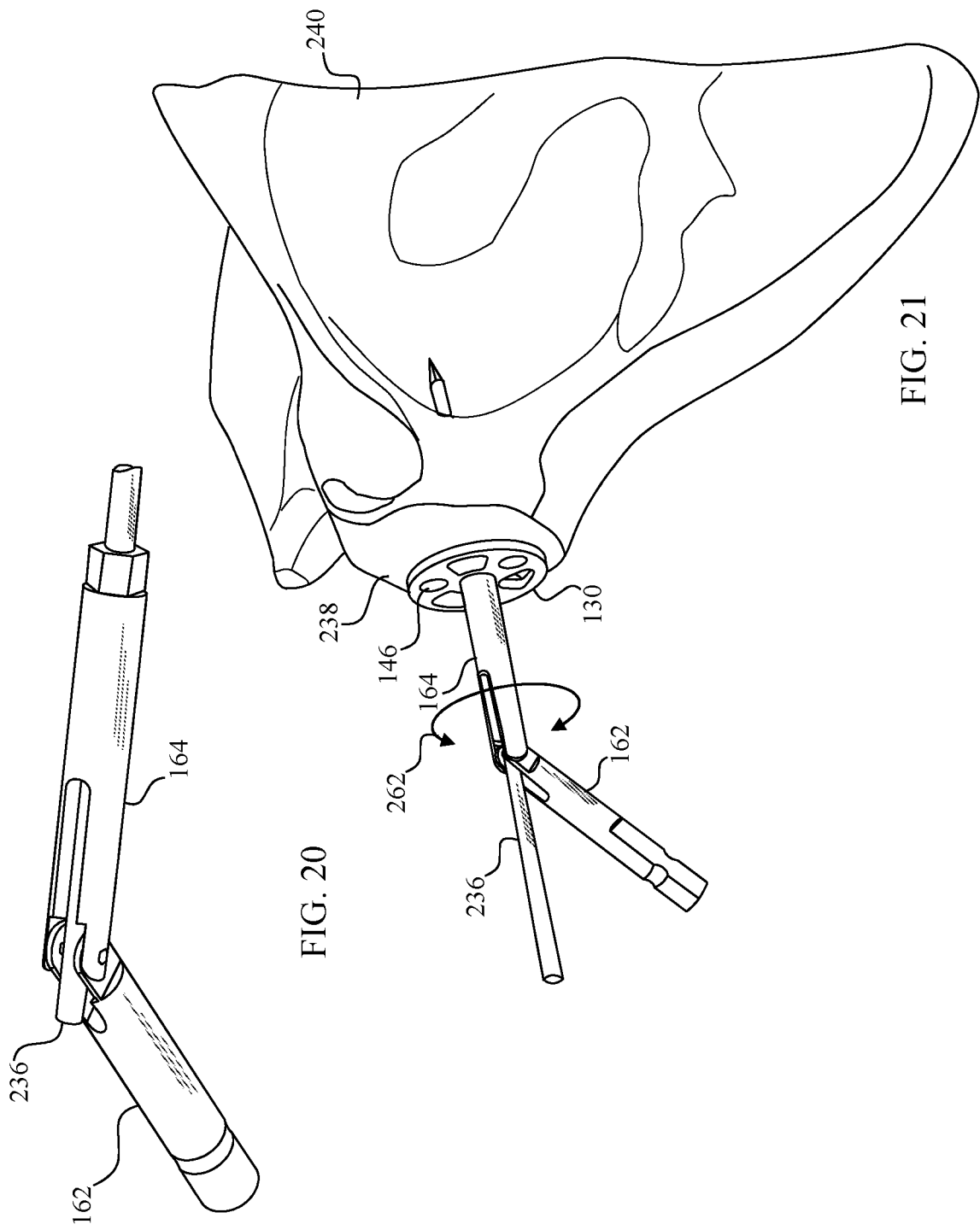

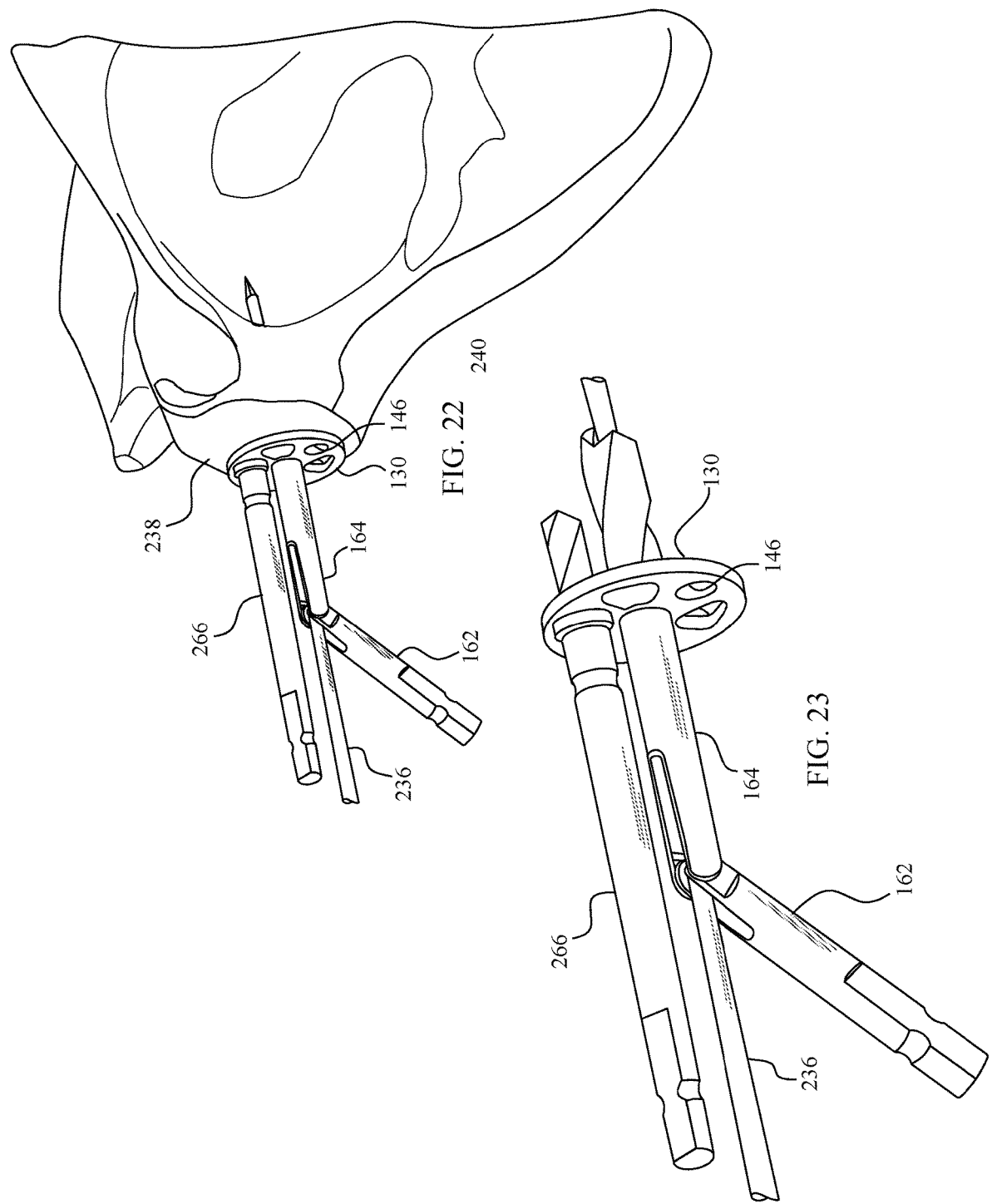

METHOD OF USING A COMBINATION DRIVER/ANTI-ROTATION HANDLE FOR SHOULDER ARTHROPLASTY

CROSS-REFERENCE TO RELATED APPLICATIONS

This application is a divisional of U.S. patent application Ser. No. 13/363,583, which was filed Feb. 1, 2012 and which issued on Sep. 19, 2017 as U.S. Pat. No. 9,763,679, which is a continuation-in-part of U.S. patent application Ser. No. 13/051,026, entitled "Combination Reamer/Drill Bit for Shoulder Arthroscopy", which was filed on Mar. 18, 2011 and which issued Nov. 21, 2017 as U.S. Pat. No. 9,820,758, the entire contents of which are each incorporated herein by reference.

TECHNICAL FIELD OF THE INVENTION

The present invention relates generally to the field of orthopedics, and, more particularly, to glenoid component apparatuses for shoulder arthroplasty and methods for using them.

BACKGROUND

As depicted in FIG. 1, a typical shoulder or glenohumeral joint is formed in a human body where the humerus 10 movably contacts the scapula 12. The scapula 12 includes a glenoid fossa 14 that forms a socket against which the head of the humerus 10 articulates. At this socket, the scapula 12 includes cartilage 16 that facilitates such articulation. Beneath the cartilage is subchondral bone 18 that forms a wall of a glenoid vault 20 that defines a cavity which contains cancellous bone 22. The subchondral bone 18 that forms the glenoid vault 20 defines a glenoid rim 24 at a periphery of the glenoid vault 20 that is attached to the cartilage 16. During the lifetime of a patient, the glenoid fossa 14 may become worn, especially at its posterior and/or superior portions thereby causing severe shoulder pain and limiting the range of motion of the patient's shoulder joint. To alleviate such pain and increase the patient's range of motion, a shoulder arthroplasty may be performed. Arthroplasty is the surgical replacement of one or more bone structures of a joint with one or more prostheses.

Shoulder arthroplasty often involves replacement of the glenoid fossa of the scapula with a prosthetic glenoid component. The conventional glenoid component typically provides a generally laterally or outwardly facing generally concave bearing surface against which a prosthetic humeral head (or, alternatively, the spared natural humeral head in the case of a glenoid hemi-arthroplasty) may bear during operation of the joint. The conventional glenoid component typically also includes a generally medially or inwardly projecting stem for fixing the glenoid component in a cavity constructed by suitably resecting the glenoid fossa 14 and suitably resecting cancellous bone 22 from the glenoid vault 20.

The goal of shoulder arthroplasty is to restore normal kinematics to the shoulder. Accordingly, known systems attempt to replicate the normal kinematics by carefully controlling the geometry of the articulating surfaces in the joint as well as the positioning of the prostheses in the bones in which the prostheses are implanted. Thus, the articulating surface of a humeral component is typically spherical and positioning of the humeral component is accomplished by using the anatomical neck of the humerus as the reference plane for reconstruction of the humeral head.

Traditionally, shoulder joints have been understood to exhibit translation of the humeral component on the glenoid component in addition to rotation. Thus, the articulating surface of the glenoid is typically formed with a radius of curvature that is much larger than the radius of curvature of the humeral component. The increased radius of curvature of the glenoid articulating surface can be from 2-6 mm larger than the radius of curvature for the humeral component in these systems.

In known systems, the glenoid component is positioned in the geometric center of the glenoid fossa. The geometric center is established by generating a line from the most superior point of the glenoid rim to the most inferior point of the glenoid rim ("Saller's line"). A second line is generated between the most posterior point of the glenoid rim and the most anterior point of the glenoid rim. The intersection of the two generated lines is considered to be the geometric center of the area circumscribed by the glenoid rim. By way of example, FIG. 2 depicts a sagittal view of the scapula 12. In FIG. 2, Saller's line 30 extends between the most superior point 32 of the glenoid rim 24 to the most inferior point 34 of the glenoid rim 24. A second line 36 extends from the most posterior point 38 of the glenoid rim 24 and the most anterior point 40 of the glenoid rim. The geometric center 42 of the glenoid fossa 14 is located at the intersection of the line 36 and Saller's line 30. As used herein, the terms anterior, posterior, superior, and inferior, unless otherwise specifically described, are used with respect to the orientation of the scapula 12 as depicted in FIG. 2.

Once a surgeon determines the placement of the glenoid component, a guide pin is positioned through the glenoid fossa. A reamer is then used to shape the scapula to receive a glenoid component, typically by forming a cavity in the glenoid vault. For glenoid components including a center peg for fixation of the glenoid component within the glenoid vault, a bore is drilled using the guide pin as a guide. The guide pin is then removed. For glenoid components including offset pegs in addition to the center peg for fixation of the glenoid component within the glenoid vault, a drill guide is introduced into the prepared cavity and additional bores are drilled for each of the offset pegs. A trial glenoid component is then implanted in the prepared cavity and, if the fit appears to be satisfactory, the trial is removed and a glenoid component is implanted in the prepared cavity.

There exists a need for a simplified method of implanting a glenoid component. There is a further need for reducing the instrumentation required to properly prepare the scapula to receive a glenoid component.

SUMMARY OF THE INVENTION

The present invention in one embodiment provides an instrumentation kit for use in preparing a bone to receive a prosthetic component which includes at least one first combination device, the at least one first combination device including a proximal portion configured to couple with a torque providing device and a distal portion configured to couple with a first instrument, the at least one first combination device pivotable between a first position whereat the proximal portion and the distal portion are (i) longitudinally aligned and (ii) configured to transfer a torque received by the proximal portion to the distal portion, and a second position whereat the proximal portion and the distal position are (i) not longitudinally aligned and (ii) configured to transfer a torque received by the proximal portion to the distal portion.

In another embodiment, a method of preparing a shoulder to receive a glenoid component includes accessing a glenoid of a shoulder, rotationally coupling a distal portion of a combination device to an instrument, applying a torque to a proximal portion of the combination device, transferring the applied torque from the proximal portion to the distal portion through a pivoting connection, rotating the instrument using the transferred applied torque, and reaming a portion of the glenoid with a rotating reaming section of the instrument using the transferred applied torque.

The above-noted features and advantages of the present invention, as well as additional features and advantages, will be readily apparent to those skilled in the art upon reference to the following detailed description and the accompanying drawings, which include a disclosure of the best mode of making and using the invention presently contemplated.

BRIEF DESCRIPTION OF THE DRAWINGS

FIG. 3 depicts a bottom perspective view of a circular glenoid component that may be implanted in a scapula in accordance with principles of the invention;

FIG. 4 depicts a bottom plan view of the circular glenoid component of FIG. 3;

FIG. 5 depicts a side plan view of the circular glenoid component of FIG. 3;

FIG. 6 depicts a side perspective view of a combination reamer/drill device that may be used to simultaneously form a bore for receiving a peg of a glenoid component and to ream a glenoid fossa to receive the glenoid component;

FIG. 7 depicts a bottom perspective view of the combination device of FIG. 6 showing the guide bore extending from a distal tip of the combination device;

FIG. 8 depicts a bottom plan view of the combination device of FIG. 6;

FIG. 9 depicts a side plan view of the combination device of FIG. 6 showing the guide bore extending to a drive section which in this embodiment is a hexagonally shaped bore in a body section of the combination device;

FIG. 10 depicts a perspective view of a combination power extension/anti-rotation handle which may be used with the combination device of FIG. 6 to couple a power rotary tool (not shown) to the combination device;

FIG. 11 depicts a bottom plan view of the combination power extension/anti-rotation handle of FIG. 10 showing a guide bore which extends from a distal tip of the lower portion;

FIG. 12 depicts a side cross sectional view of the combination power extension/anti-rotation handle of FIG. 10;

FIG. 20 depicts a perspective view of the combination power extension/anti-rotation handle after the proximal portion of the combination power extension/anti-rotation handle has been pivoted;

FIG. 21 depicts a perspective view of the scapula of FIG. 14 after the pivoted combination power extension/anti-rotation handle of FIG. 20 has been guided by the wire guide of FIG. 14 and coupled with the combination reamer/drill device of FIG. 6 allowing a user to manually orient the combination reamer/drill device on the scapula;

FIG. 22 depicts a perspective view of the scapula of FIG. 14 with the combination reamer/drill device of FIG. 6 used to guide a drill bit to form a bore to receive an offset peg of the glenoid component of FIG. 3 while the pivoted combination power extension/anti-rotation handle of FIG. 20 has been used to manually stabilize the combination reamer/drill device on the scapula; and FIG. 23 depicts a perspective view of the combination reamer/drill device of FIG. 6 and drill bit of FIG. 22 with the pivoted combination power extension/anti-rotation handle of FIG. 20.

DETAILED DESCRIPTION

Figure 1:
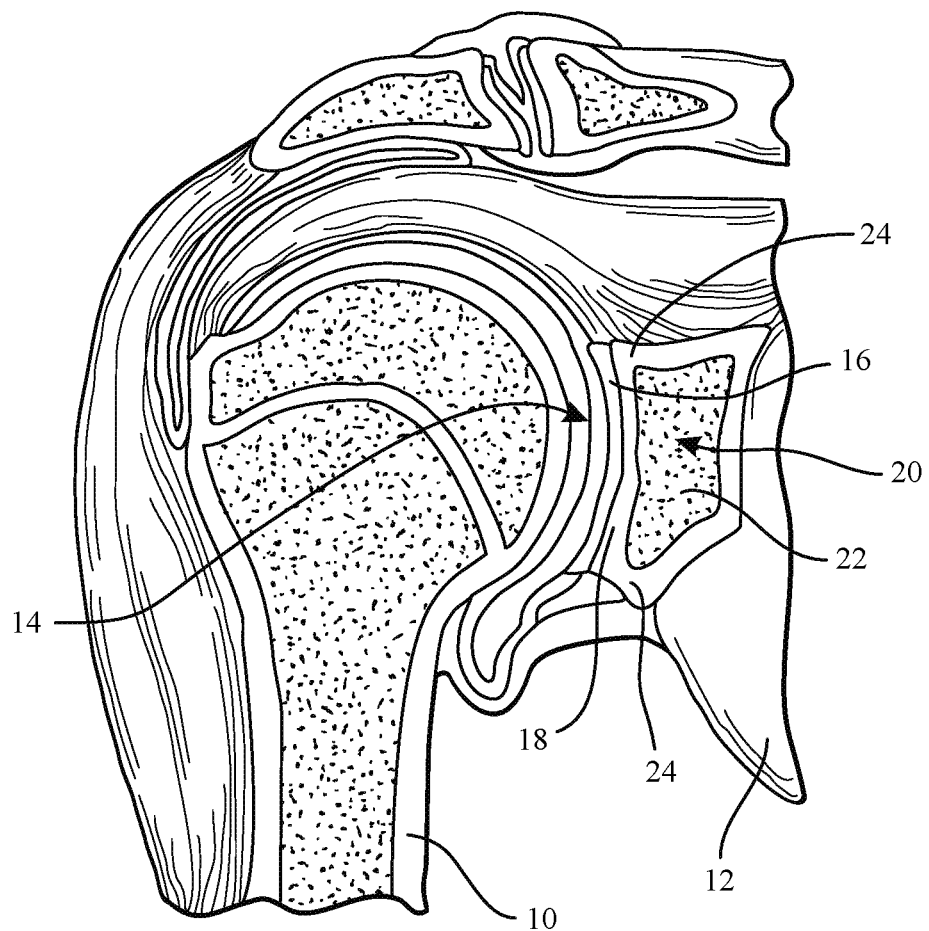
FIG. 1 depicts a coronal view of an anatomically normal shoulder joint.
Figure 2:
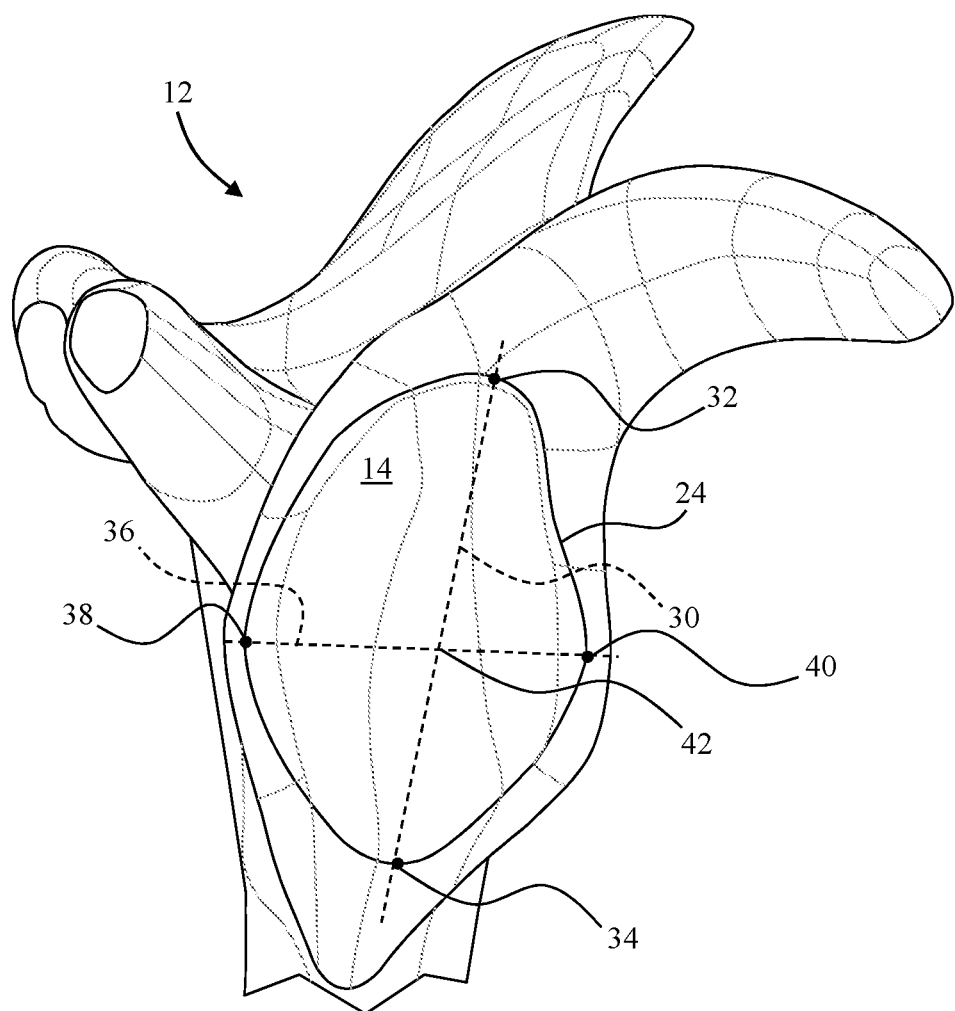
FIG. 2 depicts a sagittal view of the shoulder joint of FIG. 1.

Like reference numerals refer to like parts throughout the following description and the accompanying drawings.

FIGS. 3-5 depict a glenoid component 100. The glenoid component 100 includes a body portion 102 including a spherical articulating surface 104 and an opposite bone contacting surface 106. An outer wall 108 extends away from the bone contacting surface 106 and defines an outer periphery of the body portion 102. The bone contacting surface 106 is generally convex. A finned center peg 110 extends away from the nadir of the bone contacting surface 106 as viewed in FIG. 5. Three offset pegs 112, 114, and 116 extend away from the bone contacting surface 106 at locations between the center peg 110 and the outer wall 108. The nadir 118 of the spherical articulating surface 104 is located on the centerline 120 of the glenoid component 100.

The glenoid component 100 in this embodiment is an integrally formed unit made from a durable biocompatible plastic or any other suitable durable biocompatible material. For example, the glenoid component 100 may be made from a polyethylene. One particular polyethylene that is well suited for glenoid component 100 is a high molecular weight polyethylene, for example ultra-high molecular weight polyethylene ("UHMWPE"). One such UHMWPE is sold as by Johnson & Johnson of New Brunswick, N.J. as MARATHON™ UHMWPE and is more fully described in U.S. Pat. Nos. 6,228,900 and 6,281,264 to McKellop, which are incorporated herein by reference.

In embodiments wherein the articulating surface 104 and the other portions of the glenoid component 100 are made from different materials, the portions of the glenoid component 100 other than the articulating surface 104 may be made from a suitable biocompatible metal such as, for example, a cobalt chromium alloy, a stainless steel alloy, a titanium alloy, or any other suitable durable material. In these embodiments, the articulating surface 104 is secured to the body portion 102 in any suitable manner. For example, articulating surface 104 may be bonded to body portion 102, or articulating surface 104 could be made from polyethylene and compression molded to body portion 102. Alternately, the articulating surface 104 may be glued to the body portion 102 by, for example, an adhesive. Alternatively, articulating surface 104 may be mechanically interlocked to the body portion 102 by taper locking or otherwise press-fitting the articulating surface 104 into the body 102 and the body 102 may include any other suitable interlocking features, for example, rib(s), lip(s), detent(s), and/or other protrusion(s) and mating groove(s), channel(s), or indent(s) (not shown).

In alternative embodiments, one or more of the outer wall 108, the bone contacting surface 106, the center peg 110 and the offset pegs 112, 114, and 116 may include a porous coating to facilitate bone in-growth into the glenoid component 100. The porous coating may be any suitable porous coating and may for example be POROCOAT®, a product of Johnson & Johnson of New Brunswick, N.J. and more fully described in U.S. Pat. No. 3,855,638 to Pilliar, which is incorporated herein by reference.

In order to implant the glenoid component 100 into a scapula, the scapula must first be prepared to receive the glenoid component 100. A device which can be used to prepare the scapula to receive the glenoid component 100 is depicted in FIGS. 6-9. With reference to FIGS. 6-9, a combination reamer/drill device 130 includes a drive section 132, a body section 134, and a drill or boring section 136. The drive section 132 in this embodiment is a hexagonally shaped bore defined in the body section 134.

A number of reaming fins 140 extend from the lower central portion of the body section 134 toward the drill section 136. The reaming fins 140 curve proximally and outwardly from the lower central portion of the body section 134 to the outer periphery of the body section 134. The reaming fins 140 include an arcuate leading edge 142. The body section 134 defines a number of through-holes at locations between adjacent reaming fins 140. The through-holes in the embodiment of FIGS. 6-9 include three drill guides 146 and three ports 148.

The drill section 136 extends away from the body section 134 to a distal tip 150. Two flutes 152 and 154 extend helically about the drill section 136 between the body section 134 and the distal tip 150. A guide bore 156 extends from the distal tip 150 to the drive section 132.

As discussed in further detail below, a kit may include one or more combination reamer/drill devices 130 along with various instrumentation to facilitate use of the combination reamer/drill device 130. By way of example, FIGS. 10-12 depict a combination power extension/anti-rotation device 160 that may be included in the kit. The combination power extension/anti-rotation device 160 includes a longitudinally extending proximal portion 162 and a longitudinally extending distal portion 164. The proximal portion 162 includes a power receiving portion 166 and a junction portion 168. The power receiving portion 166 is sized and configured to couple with a power tool (not shown) and includes a pair of opposing power receiving flats 170 and a pair of coupling grooves 172 and 174 which extend about the power receiving portion 166 between the power receiving flats 170.

The junction portion 168 includes two tines 180/182 which define a receiving area 184 therebetween. A guide bore 186 extends from the receiving area 184 to the proximal tip 188 of the proximal portion 162. Two bores 190/192 extend through the respective tines 180/182.

The distal portion 164 includes a power transfer portion 200 at a distal end 202. The power transfer portion 200 is shaped to be complimentary to the drive section 132 of the combination reamer/drill 130. In the embodiment of FIGS. 10-12, the power transfer portion 200 is thus a hexagonally shaped protrusion sized to fit within the drive section 132.

A junction portion 204 is located at a proximal end 206 of the distal portion 164. The junction portion 204 includes two tines 208/210 which define an upper receiving area 212 and a lower receiving area 214 therebetween. A guide bore 216 extends from the lower receiving area 214 to the distal end 202 of the distal portion 164. Two bores 218/220 extend through the respective tines 208/210. The bores 218/220 are countersunk so that two pins 222/224 may be received therein and be flush with the outer surface of the tines 208/210.

When the combination power extension/anti-rotation handle 160 is assembled, the tines 180/182 of the proximal portion 162 are received with in the upper receiving area 212 of the distal portion 162. Additionally, the bores 190/192 are aligned with the bores 218/220, respectively. The pin 222 is positioned within the aligned bores 190/218, while the pin 224 is positioned within the aligned bores 192/220. The pins 222/224 and bores 190/192/218/220 are configured to allow the proximal portion 162 to pivot with respect to the distal portion 164 about an axis defined by the pins 222/224. To this end, the pins 222/224 in one embodiment are in the form of rivets. In another embodiment, the pins 222/224 are threadedly engaged with the bores 190/192, respectively and configured to articulate with the bores 218/220.

Additionally, the guide bore 186 and the guide bore 216 lie within the same plane when the combination power extension/anti-rotation handle 160 is assembled. As the proximal portion 162 is pivoted with respect to the distal portion 164, the guide bore 186 pivots within that same plane. Accordingly, the guide bores 186 and 216 may be pivoted into alignment with each other. When the guide bores 186 and 216 are aligned, the proximal portion 162 and the distal portion 164 are longitudinally aligned as depicted in FIG. 10.

Figure 13:
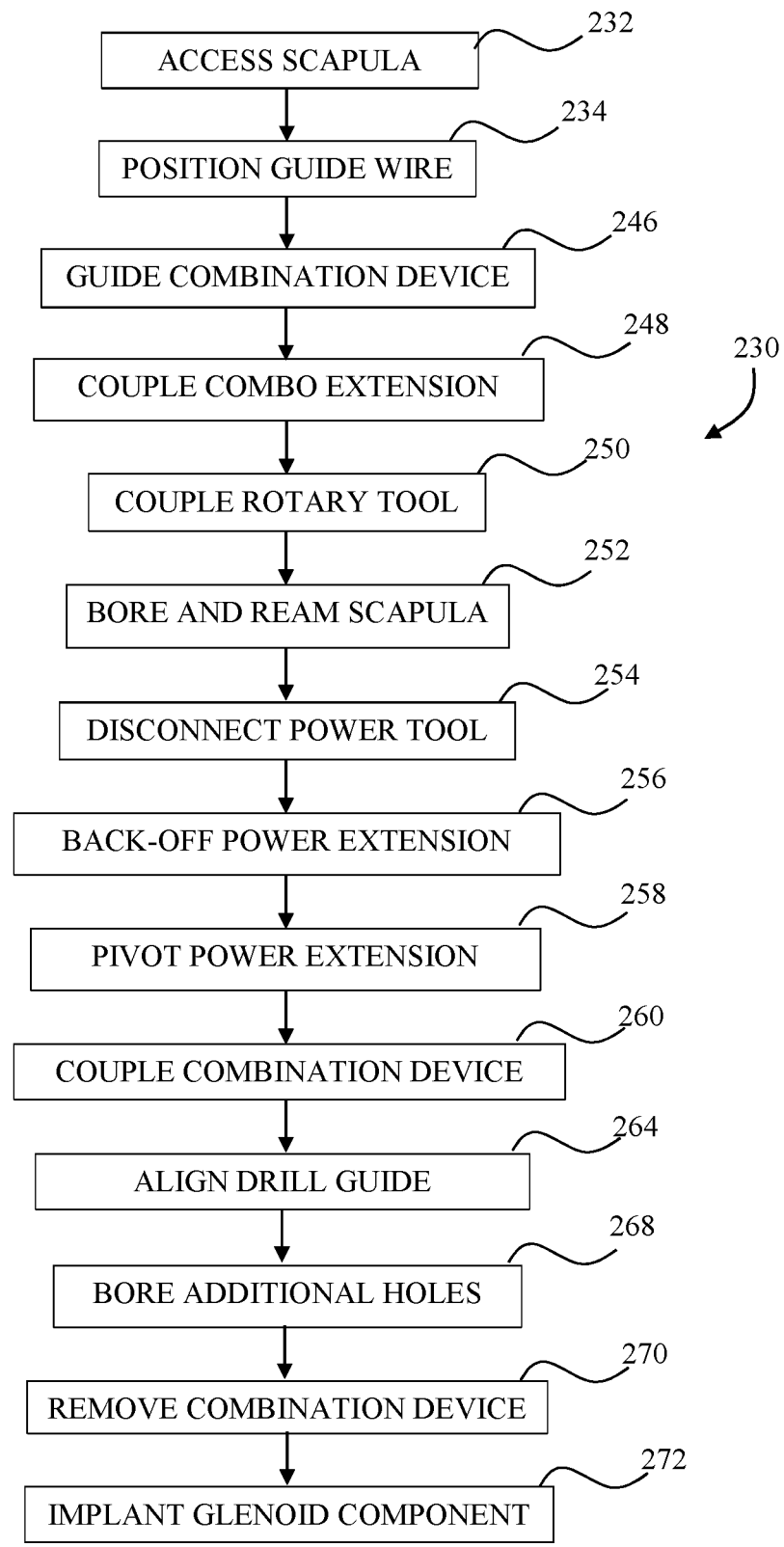
FIG. 13 depicts a medical procedure that may be used to implant the circular glenoid component of FIG. 3 into a scapula using the combination device of FIG. 10.
Figure 14:
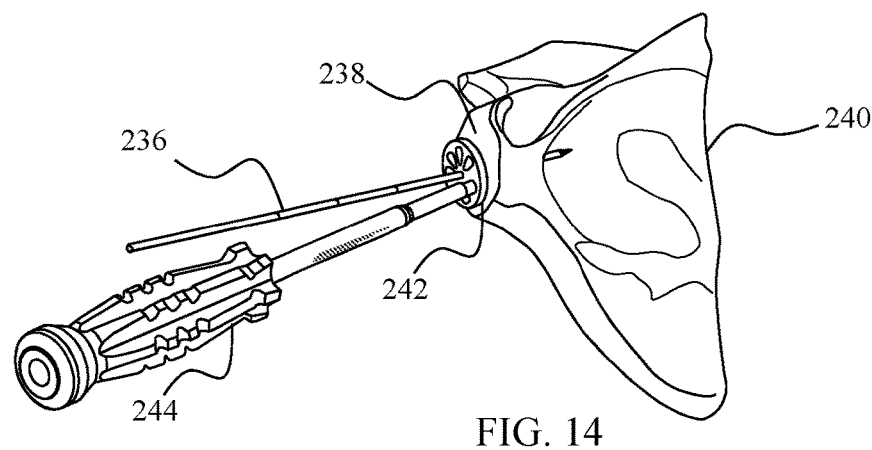
FIG. 14 depicts a perspective view of the scapula of FIG. 2 with a guide wire positioned in the scapula using a guide template and a guide template manipulator.

A kit including the combination reamer/drill device 130 and the power extension/anti-rotation handle 160 may be used in preparing a shoulder to receive a glenoid component such as glenoid component 100 in accordance with a procedure 230 depicted in FIG. 13. Initially, a scapula is accessed at block 232 in accordance with a desired surgical approach. At block 234, a guide wire, which may be provided in a kit along with other instrumentation used in the procedure 230, is positioned on the scapula. Positioning of the guide wire may be computer aided. In one embodiment, the guide wire is positioned based upon identification of the center of an inferior glenoid circle. By way of example, FIG. 14 depicts a guide wire 236 implanted into a glenoid 238 of a scapula 240. In the embodiment of FIG. 20, the guide wire 236 has been positioned with the aid of a guide plate 242 and a guide plate manipulator 244.

Figure 15:
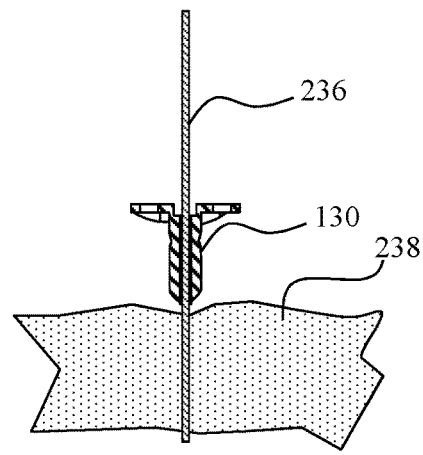
FIG. 15 depicts a partial cross-sectional view of the scapula of FIG. 14 with the combination reamer/drill device of FIG. 6 guided to a location adjacent to the glenoid fossa by the guide wire of FIG. 14.

Once the guide wire is positioned, a combination reamer/drill device 130 is positioned with the guide bore 156 aligned with the guide wire 236. The combination reamer/drill device 130 is then moved toward the guide wire 236 and at block 246 the guide wire 236 is used to guide the combination reamer/drill device 130 to a location adjacent to the glenoid 238 of the scapula 240 as depicted in FIG. 15.

Figure 16:
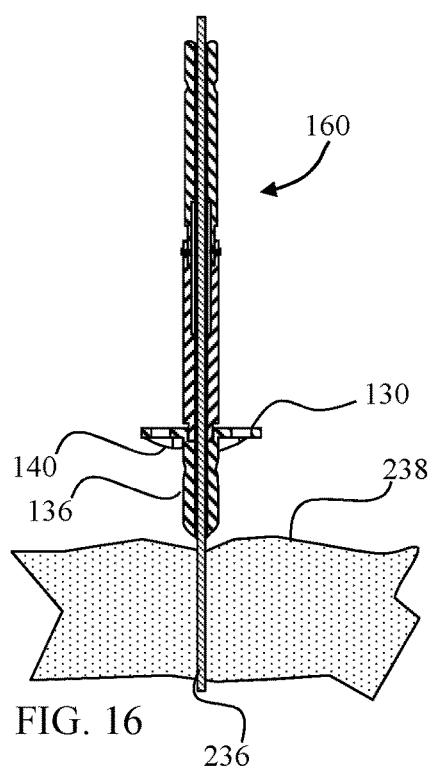
FIG. 16 depicts a partial cross-sectional view of the scapula of FIG. 14 with the combination power extension/anti-rotation handle of FIG. 10 coupled to the combination reamer/drill device of FIG. 6, both the combination power extension/anti-rotation handle and the combination reamer/drill device guided to a location adjacent to the glenoid fossa by the guide wire of FIG. 14.

At block 248, a combination power extension/anti-rotation handle 160 is coupled to the combination device 130 by first aligning the guide bore 216 (see FIG. 12) with the guide wire 236. The combination power extension/anti-rotation handle 160 is then moved over the guide wire 236 until the guide wire 236 extends through the guide bore 216 and into the lower receiving area 214. The proximal portion 162 is then pivoted with respect to the distal portion 164 as necessary to align the guide bore 186 with the guide wire 236. The combination power extension/anti-rotation handle 160 is then moved over the guide wire 236 until the power transfer portion 200 is adjacent to the drive section 132 of the combination reamer/drill device 130. If needed, the combination power extension/anti-rotation handle 160 is rotated on the guide wire 236 to rotationally align the shaped power transfer portion 200 with the shaped drive section 132 and the power transfer portion 200 is inserted into the drive section 132 resulting in the configuration of FIG. 16.

A rotary tool (not shown) is then coupled to the combination power extension/anti-rotation handle 160 at block 250. Thus, the rotary tool is coupled to the power receiving portion 166 of the proximal portion 162 so as to be indirectly coupled to the combination reamer/drill device 130.

Power is then applied to the rotary tool causing the rotary tool to rotate the combination power extension/anti-rotation handle 160. Rotary force is transferred to the drive section 132 of the combination reamer/drill device 130 through the power transfer portion 164 (see FIG. 12). More specifically, torque is passed from the rotary tool to the power receiving portion 166. The tines 180/182/208/210 are configured such that the torque received by the proximal portion 162 is transferred to the tines 208/210 through the tines 180/182. The torque is then transferred from the power transfer portion 200 to the drive section 132, causing the combination reamer/drill device 130 to rotate.

Figure 17:
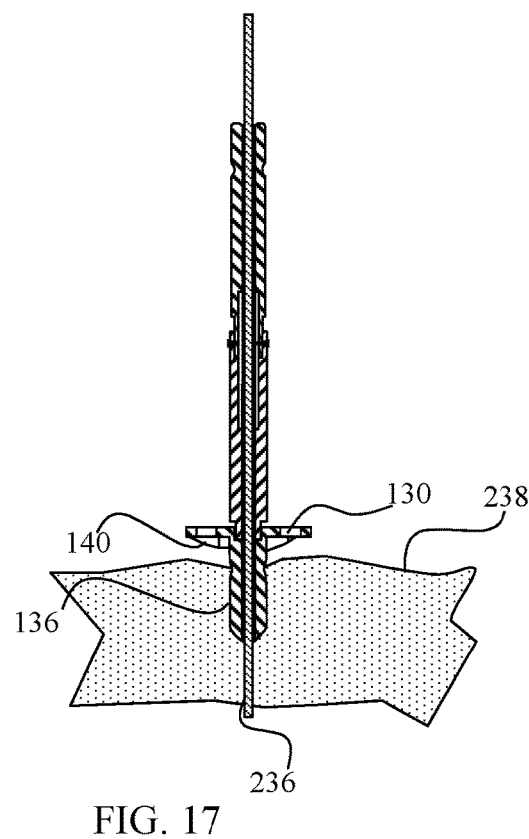
FIG. 17 depicts a partial cross-sectional view of the scapula of FIG. 14 and the coupled combination power extension/anti-rotation handle and the combination reamer/drill devices of FIG. 16 after the combination reamer/drill device has been used to form a bore in preparation for implanting the glenoid component of FIG. 3 into the scapula.
Figure 18:
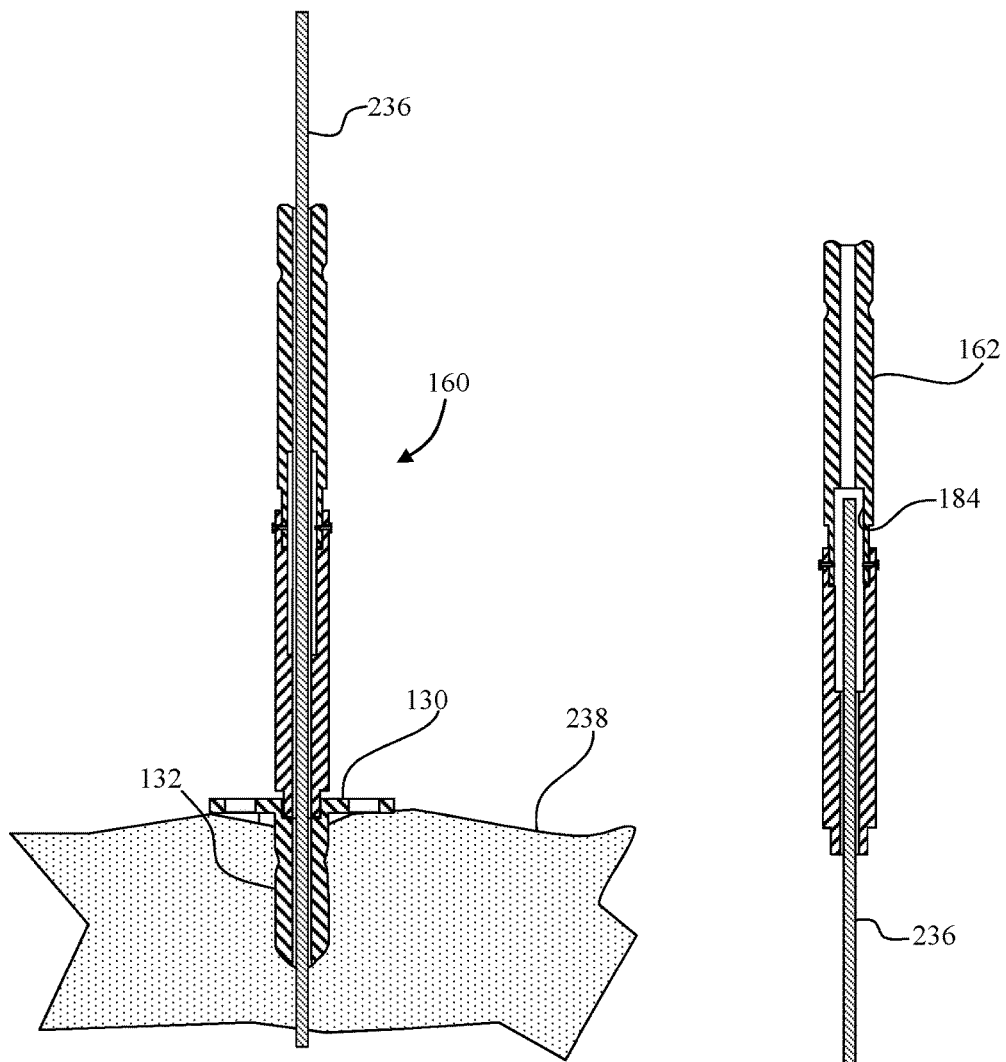
FIG. 18 depicts a partial cross-sectional view of the scapula of FIG. 14 and the coupled combination power extension/anti-rotation handle and the combination reamer/drill devices of FIG. 16 after the combination reamer/drill device has been used to simultaneously ream the glenoid fossa and form a bore in preparation for implanting the glenoid component of FIG. 3 into the scapula.

As the combination reamer/drill device 130 initially rotates about the guide wire 236, the drill section 136 contacts the glenoid 238 and begins to bore a hole in the glenoid 238. The reaming fins 140, however, are initially spaced apart from the glenoid 238 as depicted in FIG. 17. Accordingly, no reaming occurs. As a hole is formed in the glenoid 238 by the drill section 136, the combination reamer/drill device 130 is guided by the guide wire 236 such that the reaming fins 140 come into contact with the glenoid 238 as depicted in FIG. 18. Continued rotation of the combination reamer/drill device 130 with the rotary tool thus causes simultaneous reaming of the glenoid 238 with the reaming fins 140 and boring of the scapula 240 with the drill section 136 at block 252.

Once the glenoid 238 has been reamed to the desired depth, the power tool is de-energized and disconnected at block 254. The size of the drill section 132, both in length and diameter, is selected to be complimentary to the size of the center peg 110 of the glenoid component 100. Thus, upon completion of the reaming, the bore formed by the drill section 132 is sized to receive the finned center peg 110.

Figure 19:
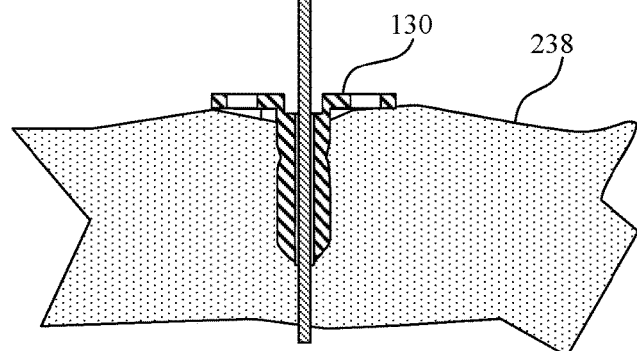
FIG. 19 depicts a perspective view of the scapula of FIG. 14 after the combination power extension/anti-rotation handle has been withdrawn along the guide wire 236 to a location that allows pivoting of the proximal portion of the combination power extension/anti-rotation handle.

The combination power extension/anti-rotation handle 160 is then backed away from the combination reamer/drill device 130 along the guide wire 236 at block 256 until the end of the guide wire 126 is located within the receiving area 184 of the proximal portion 162 resulting in the configuration of FIG. 19. While the guide wire was within the guide bore 186 of the proximal portion 162, the proximal portion 162 was maintained in alignment with the distal portion 164 which enables smooth transfer of torque through the combination power extension/anti-rotation handle 160. Once the guide wire 236 is no longer within the guide bore 186, however, the proximal portion 162 may be pivoted with respect to the distal portion 164 to the configuration of FIG. 20 (block 258).

At block 260, the combination power extension/anti-rotation handle 160 is coupled to the combination device 130 substantially in the manner described above. Since the guide wire 236 does not extend through the proximal portion 162, however, the proximal portion 162 may be used as a handle to rotate the coupled combination power extension/anti-rotation handle 160 and combination reamer/drill device 130 about an axis defined by the guide wire 236 as indicated by the arrow 262 of FIG. 21. The combination power extension/anti-rotation handle 160 is thus used to align a drill guide 146 in the combination reamer/drill device 130 with a desired location (block 264). In one embodiment, a handle similar to the handle shown attached to the guide plate manipulator 244 of FIG. 14 may be included in the kit. Such a handle may be removably coupled to the power receiving portion 166 of the proximal portion 162 to facilitate manipulation of the combination power extension/anti-rotation handle 160.

The ability to pivot the proximal portion 162 provides a surgeon with a relatively unobstructed view of the combination reamer/drill device 130. Accordingly, the surgeon may view the reamed surface of the glenoid 238 through the drill guides 146. This allows a surgeon to view the location in the scapula 240 at which the offset fixation pegs 112, 114, and 116 of the glenoid component 100 will be anchored. In the embodiments in this example wherein the number and positioning of the drill guides 146 are complimentary to the number and positioning of the offset fixation pegs 112, 114, and 116, the surgeon may orient the combination reamer/drill device 130 such that each of the drill guides 146 is aligned with portions of the scapula 240 that can provide a good anchor for the offset fixation pegs 112, 114, and 116.

Once the combination reamer/drill device 130 is aligned at the block 264, a drill bit is inserted through one of the drill guides 146 to drill an additional bore at a location spaced apart from the first bore formed using the drill section 136 at block 230. By way of example, FIGS. 22 and 23 depict a drill bit 266 positioned in a drill guide 146 of the combination device 130. The combination power extension/anti-rotation handle 160 may be used to steady the combination reamer/drill device 130 during the drilling process. The offset of the proximal portion 162 from the axis defined by the wire guide 236 results in a mechanical advantage in maintaining the combination reamer/drill device 130 at the desired orientation. Blocks 264 and 268 may be repeated as desired to form additional holes.

Once all of the desired holes are formed, the combination reamer/drill device 130 is removed at block 270. The combination power extension/anti-rotation handle 160 may be used to aid in removal of the combination reamer/drill device 130. At block 272, the glenoid component is implanted. In this example, the glenoid component 100 has a lower bone contacting surface 106 shaped complimentary to the reaming cross-section of the reaming fins 140. Thus, in this example the lower bone contacting surface 106 is curved complimentary to the distal curve of the reaming fins 140. In other embodiments, the reaming fins 140 may be configured to produce a flat bottomed area if a glenoid component with a flat lower bone contacting surface is used. Accordingly, a kit in one embodiment includes different combination devices with differently shaped reaming cross-sections.

Moreover, while in the embodiment of FIGS. 10-12 the proximal portion 162 is only pivotably connected to the distal portion 164, in another embodiment the proximal portion is both pivotably and slidably connected to the distal portion. This can be accomplished by providing longitudinal slots connected to the bores 218/220. In this embodiment, once the proximal portion is aligned with the distal portion, the proximal portion may be moved toward the distal portion. Accordingly, in addition to torque being passed through the tines in the junction portion, additional features may be incorporated in the proximal and distal portions which are selectively interlocked. This arrangement allows for a more robust connection between the proximal portion and the distal portion which is useful in embodiments wherein weaker materials are desired to be used in forming a combination power extension/anti-rotation handle.

In yet another embodiment, the guide bores in the proximal portion and the distal portion are positioned substantially immediately adjacent to one another when the proximal and distal portions are aligned. In this embodiment, pivoting between the proximal and distal portions is enabled by moving the combination power extension/anti-rotation handle such that the wire guide does not extend into the guide bore in the proximal portion.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

What is claimed is:

1. A method of preparing a shoulder to receive a glenoid component comprising:
   accessing a glenoid of a shoulder;
   rotationally coupling a distal portion of a combination power extension/anti-rotation device to an instrument;
   applying a torque to a proximal portion of the power extension/anti-rotation combination device;
   transferring the applied torque from the proximal portion to the distal portion through a pivotable connection;
   rotating the instrument using the transferred applied torque; and reaming a portion of the glenoid with a rotating reaming section of the instrument using the transferred applied torque;
   pivoting the proximal portion with respect to the distal portion after reaming the portion of the glenoid;
   rotating the instrument to a first position using the pivoted proximal portion; and
   forming a first bore in the glenoid with the instrument positioned against the glenoid and rotated to the first position.

2. The method of claim 1, further comprising:
   maintaining the instrument at the first position using the pivoted proximal portion while forming the first bore.

3. The method of claim 1, further comprising:
   identifying a first offset fixation peg location on the glenoid through a first drill guide extending through a body portion of the instrument and located proximal the reaming portion prior to forming the first bore, wherein:
   forming the first bore further comprises forming the first bore at the identified first offset fixation peg location.

4. Then method of claim 3, wherein the instrument further includes a second drill guide extending through the body portion of the instrument, the method further comprising:
   identifying a second offset fixation peg location on the glenoid through the second drill guide; and
   forming a second bore at the identified second offset fixation peg location using the second drill guide.

5. Then method of claim 4, wherein the instrument further includes a third drill guide extending through the body portion of the instrument, the method further comprising:
   identifying a third offset fixation peg location on the glenoid through the third drill guide; and
   forming a third bore at the identified third offset fixation peg location using the third drill guide.

6. The method of claim 1, wherein rotating the instrument to the first position using the pivoted proximal portion comprises:
   rotating the instrument about a wire guide extending through the distal portion.

7. The method of claim 1, further comprising, prior to applying the torque to the proximal portion of the combination power extension/anti-rotation device:
   positioning a wire guide in the shoulder; and
   positioning the instrument and the combination power extension/anti-rotation device such that the wire guide extends through a first guide bore in the instrument, a second guide bore in the distal portion, and a third guide bore in the proximal portion.

8. The method of claim 7, wherein pivoting the proximal portion with respect to the distal portion comprises:
   moving the proximal portion away from the instrument so that the wire guide is no longer within the third guide bore.

9. The method of claim 8, wherein pivoting the proximal portion with respect to the distal portion further comprises:
   pivoting the proximal portion about a pin extending through a first tine of the proximal portion and a second tine of the distal portion after moving the proximal portion away from the instrument so that the wire guide is no longer within the third guide bore.

10. The method of claim 9, wherein moving the proximal portion away from the instrument decouples the distal portion of the combination device and the instrument, the method further comprising:
    moving the distal portion along the guide wire toward the instrument using the pivoted proximal portion;
    rotationally aligning the distal portion and the instrument using the pivoted proximal portion; and
    recoupling the distal portion and the instrument using the pivoted proximal portion.

* * * * *